United States Patent
Solomon et al.

(10) Patent No.: US 6,818,718 B2
(45) Date of Patent: Nov. 16, 2004

(54) ELECTROPHORESIS GELS AND CROSS-LINKING AGENTS FOR THEIR PREPARATION

(75) Inventors: David Henry Solomon, Officer (AU); Grace Chan, Marsfield (AU); Peter Agapitus Kambouris, Box Hill North (AU); Mark Graham Looney, Brunswick (AU)

(73) Assignee: The University of Melbourne, Parkville (AU)

( * ) Notice: Subject to any disclaimer, the term of this patent is extended or adjusted under 35 U.S.C. 154(b) by 684 days.

(21) Appl. No.: 09/740,928

(22) Filed: Dec. 21, 2000

(65) Prior Publication Data

US 2001/0020079 A1 Sep. 6, 2001

Related U.S. Application Data

(62) Division of application No. 09/214,716, filed as application No. PCT/AU97/00437 on Jul. 10, 1997, now Pat. No. 6,197,906.

(30) Foreign Application Priority Data

Jul. 10, 1996 (AU) ............................................. PO0932

(51) Int. Cl.$^7$ ................................................. C08F 12/30
(52) U.S. Cl. ........................................ 526/286; 204/469
(58) Field of Search ............................. 526/286; 435/4, 435/6; 204/456, 466, 469

(56) References Cited

U.S. PATENT DOCUMENTS

| | | |
|---|---|---|
| 3,645,984 A | 2/1972 | Dowbenko et al. |
| 3,857,824 A | 12/1974 | Atkins |
| 3,933,754 A | 1/1976 | Kitagawa |
| 4,074,039 A | 2/1978 | Lim |
| 4,101,461 A | 7/1978 | Strop |
| 4,104,208 A | 8/1978 | Kido |
| 4,417,034 A | 11/1983 | Webster |
| 4,963,243 A | 10/1990 | Ogawa |
| 5,147,394 A | 9/1992 | Siepser |
| 5,300,537 A | 4/1994 | Muller et al. |
| 5,405,366 A | 4/1995 | Fox |

FOREIGN PATENT DOCUMENTS

| | | |
|---|---|---|
| AU | 40206/95 A | 6/1996 |
| EP | 0 330 460 A2 | 8/1989 |
| EP | 510 646 A | 10/1999 |
| GB | 989201 | 4/1965 |
| GB | 1259609 * | 1/1972 |
| GB | 4417034 | 11/1983 |
| GB | 5300537 | 4/1994 |

OTHER PUBLICATIONS

Patent Abstracts of Japan, Takashi, Y., "Polymerizable Compound Containing Aryloyloxy Group and . . . ," Publication No. 01087608 dated Mar. 31, 1989.
Chemical Abstract No. 99:128329, "Soft contact lenses absorbing a large amount of water".
Chemical Abstracts, Abstract No. 99: 128392, JP 58 028 718 A2 (Toyo Contact Lens Co., Ltd) Feb. 19, 1983 Abstract.
Chemical Abstracts, Abstract No. 99:54494, JP 58 029 744 A2 (Toyo Contact Lens Co., Ltd) Feb. 22, 1983 Abstract.

* cited by examiner

*Primary Examiner*—Edward J. Cain
(74) *Attorney, Agent, or Firm*—Nixon & Vanderhye

(57) ABSTRACT

Method of separating molecules by providing a cross-linked polymer gel having a cross-linking moiety of the formula

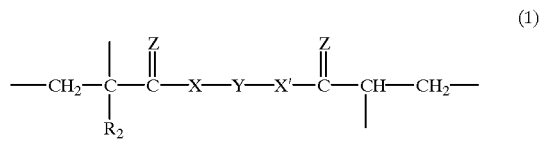

(1)

wherein X, X', Y, Z and $R_2$ are as defined in the specification. A sample containing the molecules to be separated is placed on the gel, and the gel is subjected to a separation technique.

3 Claims, 2 Drawing Sheets

A

B

C

D

D

C

B

A

ELECTROPHORESIS GELS AND CROSS-LINKING AGENTS FOR THEIR PREPARATION

This is a divisional of application Ser. No. 09/214,716, filed Feb. 18, 1999, now U.S. Pat. No. 6,197,906, which is a 371 of PCT/AU97/00437 filed Jul. 10, 1997, the entire content of which is hereby incorporated by reference in this application.

TECHNICAL FIELD

This invention relates to the separation of molecules on polymer gels, in particular to the preparation of novel crosslinked polymer gels, the separation of molecules by techniques such as electrophoresis using these gels, novel crosslinking agents useful in the preparation of the gels, and novel intermediates useful in the synthesis of the crosslinking agents. The invention is especially suitable for electrophoretic applications and accordingly, for convenience, the invention will be further described with reference to electrophoresis. It is to be understood, however, that the gels, processes and crosslinking agents of the present invention are not so limited.

BACKGROUND OF INVENTION

Polyacrylamide gel electrophoresis is an analytical technique whereby fragments of biomolecules, such as DNA, enzymes and proteins, may be separated and identified on the basis of their molecular size, weight and charge. Commercially available electrophoresis gels have conventionally been produced by copolymerisation of acrylamide with the symmetrical crosslinking agent, N,N'-methylene bisacrylamide, otherwise known as BIS. Since both double bonds of BIS are of the same type their reactivities are essentially the same. Other known crosslinking agents include ethylene glycol diacrylate, dihydroxy ethylenebisacrylamide (DHEBA), N,N'-propylenebisacrylamide, diacrylamide dimethylether, 1,2-diacrylamide ethyleneglycol, ethyleneureabisacrylamide, N,N'-bisacrylylcystamine and bisacrylamide methylether (BAME). As for BIS, the double bonds of these crosslinking agents are of the same type.

DISCLOSURE OF INVENTION

It has now been found that electrophoresis gels having surprisingly improved separating ability can be prepared using particular asymmetrical crosslinking agents.

Accordingly the invention provides a crosslinked polymer gel comprising a crosslinking moiety of the formula:

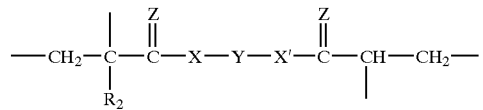

wherein X and X' are independently selected from the group consisting of —O—, —S— and —NR—, where R is H, alkyl or cycloalkyl, $R_2$ is a $C_1$–$C_4$ alkyl group, Y is an optionally substituted non-aromatic divalent linking group, and Z is O or S.

Preferably $R_2$ is $CH_3$.

The monomer or monomers used to prepare the gel may be any suitable monomer.

The crosslinked polymer gel may be prepared from monomers having the formula $H_2C=CR_5$—CO—$NR_3R_4$ where $R_3$, $R_4$ and $R_5$ are each independently H or alkyl optionally monosubstituted by, for example, OH or $C(O)CH_2C(O)CH_3$. Examples of monomers include acrylamide, acrylamide derivatives or acrylamide substitutes known to the art such as N,N-dimethylacrylamide, methacrylamide, methyloylacrylamide, propylacrylamide, dipropyl acrylamide, isopropyl acrylamide, diisopropyl acrylamide, lactyl acrylamide, methoxyacrylamide and mixtures thereof. Preferably the monomer is acrylamide.

The linking group may be any suitable non-aromatic hydrocarbyl group, optionally including one or more heteroatoms selected from O, S, N and P.

Preferably X and X' are the same. Preferably Z is oxygen.

In another aspect of the invention there is provided a method of preparing a crosslinked polymer gel, said method including the step of subjecting one or more monomers to crosslinking polymerisation with one or more crosslinking agents of the formula I:

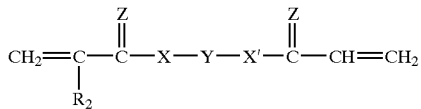

wherein X and X' are independently selected from the group consisting of —O—, —S— and —NR—, where R is H, alkyl or cycloalkyl, $R_2$ is a $C_1$–$C_4$ alkyl group, Y is an optionally substituted non aromatic divalent linking group, and Z is O or S.

$R_2$ is preferably $CH_3$.

The polymer gels according to the present invention may be prepared using one or more crosslinking agents of formula I, optionally in the presence of one or more conventional crosslinking agents known to the art. Preferably the crosslinking agent(s) is/are selected to provide a gel which is substantially transparent to visible light. Preferably the gel is an aqueous gel.

The polymer gels according to the present invention are useful for separating molecules, especially charged species, or species capable of bearing a charge such as biomolecules.

The polymer gel may be an electrophoretic gel. The electrophoretic gel may have a porosity gradient suitable for gradient gel electrophoresis. See for example, *Polyacrylamide Gel Electrophoresis across a Molecular Sieve Gradient* Margolis, J., Kenrick, K. G., Nature, 214, 1967, p1334–1336; *Polyacrylamide Gel Electrophoresis in a Continuous Molecular Sieve Gradient*, Margolis, J., Kenrick, K. G., Analytical biochemistry, 25, 1968, p347–362; and *Practical System for Polyacrylamide Gradient Gel electrophoresis*, Margolis, J., Laboratory Practice, 22, p107–109, 1973, the disclosures of which are incorporated herein by reference.

In a further aspect the invention provides a method of separating molecules comprising:

providing a crosslinked polymer gel by combining one or more monomers with a crosslinking agent of the formula I:

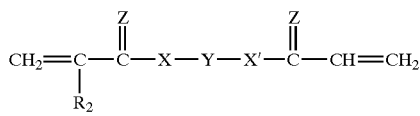

wherein X and X' are independently selected from the group consisting of —O—, —S— and —NR—, where R is H, alkyl or cycloalkyl, R$_2$ is a C$_1$–C$_4$ alkyl group, and Y is an optionally substituted non aromatic divalent linking group, and Z is O or S, optionally in the presence of an initiator, subjecting the monomer solution to polymerisation and crosslinking, placing a sample containing the molecules to be separated onto the gel, and subjecting the gel and sample to a separation technique. Preferably the separation technique is electrophoresis. The electrophoresis technique employed may be any of those known to the art, including one-, two- and multi-dimensional techniques. The electrophoresis technique may be gradient gel electrophoresis.

Preferably polymerisation is carried out on a solution of the monomer or monomers with the crosslinking agent.

The linking group is preferably selected to provide a crosslinking agent which is soluble in the monomer solution. For most applications involving acrylamide the solvent will be water, and accordingly it is preferred that the linking group is selected to provide a crosslinking agent which is soluble in water or water/acrylamide. Other solvents include DMF, THF, alcohols and other water miscible systems.

Where the solvent is water and/or the monomer is acrylamide, the hydrophilic/lipophilic balance of the linking group may be controlled so that the cross-linking agent is soluble in water or water/acrylamide. Accordingly if the linking group contains a large number of carbon atoms (eg. more than about 7) the effect on solubility can be offset by including sufficient oxygen atoms or other polar groups to provide a crosslinking agent which is soluble in the acrylamide/water solution.

Examples of divalent linking groups include alkylene, oxyalkylene, polyoxyalkylene, cycloalkylene, alkanedioyl, alkylenedisulphonyl, alkylenecarbonyl, thioalkylene, ureylene, oxalyl, aminoalkylene, alkylenedisulphonyl, heterocyclyl and groups of the formula —(R$^1$)$_m$—R$^2$—(R$^3$)$_n$—, where R$^1$ and R$^3$ are selected from alkylene, cycloalkylene, heterocyclyl, oxyalkylene, polyoxyalkylene, alkylenecycloalkylene and alkyleneheterocyclyl; R$^2$ is selected from a direct bond, —O—, —S—, —S—S—, alkylene, alkanedioyl, alkylenedioxy, alkylenedisulphonyl, —NR—, —NRC(O)O—, —NR—C(O)—NR—, —NRC(O)—, —N=N—, —NRC(O)C(O)—NR—, —C(O)—, —C(S)— and —RNNR—, where R is H, alkyl or cycloalkyl; m and n are 0 or 1 provided that m+n≠0.

As used herein the term "non-aromatic hydrocarbyl group" means any divalent group comprising carbon and hydrogen which does not include an aromatic or heteroaromatic ring.

As used herein the term "alkylene", used either alone or in compound words such as "oxyalkylene", "carbonylalkylene" denotes straight chain and branched C$_{1-10}$ alkylene groups. Examples include methylene, ethylene, propylene, isopropylene, butylene, isobutylene, sec-butylene, pentylene, isopentylene, sec-pentylene, 1,2-dimethylpropylene, 1,1-dimethylpropylene, hexylene, 4-methylpentylene, 1-methylpentylene, 3-methylpentylene, 1,1-dimethylbutylene, 2,2-dimethylbutylene, 3,3-dimethylbutylene, 1,2-dimethylbutylene, 1,3-dimethylbutylene, 1,2,2-trimethylpropylene, 1,1,2-trimethylpropylene, heptylene, 5-methylhexylene, 1-methylhexylene, 2,2-dimethylpentylene, 3,3-dimethylpentylene, 4,4-dimethylpentylene, 1,2-dimethylpentylene, 1,3-dimethylpentylene, 1,4-dimethylpentylene, 1,2,3-trimethylbutyl, 1,1,2-trimethylbutylene and the like.

The term "cycloalkylene", used alone or in compound words such as "alkylenecycloalkylene" denotes divalent cyclic C$_{3-7}$ alkyl groups. Examples include cyclopropyl, cyclobutyl, cyclopentyl and cycloheptyl.

The term "heterocyclyl" as used alone or in compound names such as "alkyleneheterocyclyl" denotes 5 or 6 membered heterocyclic rings. Examples of 5 or 6 membered heterocyclic rings include pyrrolidine, imidazolidine, pyrazolidine, thiazolidine, isothiazolidine, oxazolidine, piperidine and piperazine.

In this specification the term "optionally substituted" means that a group may or may not be further substituted with one or more groups selected from alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenacyl, alkynylacyl, acylamino, diacylamino, acyloxy, alkylsulphonyloxy, heterocyclyl, heterocycloxy, heterocyclamino, haloheterocyclyl, alkylsulphenyl, carboalkoxy, alkylthio, acylthio, phosphorous-containing groups such as phosphono and phosphinyl, and groups of the formula

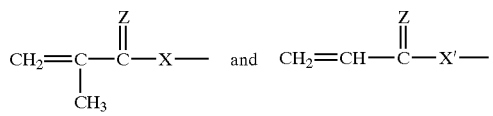

where X, X' and Z are as defined above.

The term "alkyl", used either alone or in compound words such as "haloalkyl" or "alkylthio", denotes straight chain or branched C$_{1-6}$ alkyl groups. Examples include methyl, ethyl, propyl, isopropyl and the like.

The term "alkoxy" denotes straight chain or branched alkoxy. preferably C$_{1-10}$ alkoxy. Examples include methoxy, ethoxy, n-propoxy, isopropoxy and the different butoxy isomers.

The term "alkenyl" denotes groups formed from straight chain, branched or mono or polycyclic alkenes including ethylenically mono- or poly-unsaturated alkyl or cycloalkyl groups as previously defined, preferably C$_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cyclooctatetraenyl.

The term "halogen" denotes fluorine, chlorine, bromine or iodine, preferably chlorine or fluorine.

The term "acyl" used either alone or in compound words such as "acyloxy", "acylthio", "acylamino" or "diacylamino" denotes carbamoyl, aliphatic acyl group and acyl group containing a heterocyclic ring which is referred to as heterocyclic acyl, preferably $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopropylcarbonyl cyclobutylcarbonyl, cyclopentylcarbonyl or cyclohexylcarbonyl; alkylsulfonyl, such as methylsulfonyl or ethylsulfonyl; alkoxysulfonyl, such as methoxysulfonyl or ethoxysulfonyl; heterocyclylcarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

The term "biomolecule" as used herein denotes biological molecules such as proteins, enzymes and other peptides, genetic material such as chromosomal material, genomic DNA, cDNA, mRNA, tRNA and other oligo- and polynucleotides. The term includes naturally occurring biological molecules in addition to fragments and recombinant derivatives thereof.

The divalent linking group Y may be saturated or mono-, di- or poly-unsaturated. Accordingly, the group Y may be any of the linking groups described above in which one or more of carbon-to-carbon single bonds is replaced by a double bond. For example the divalent linking group may further include alkenylene moieties such as butenylene; cycloalkenylene moieties such as 1-cyclohexenylene, alkenedioyl moieties such as fumaryl, maleyl, citraconyl and mesaconyl: heterocyclyl moieties such as pyrroline, imidazoline, pyrazoline and oxazoline.

Other suitable divalent linking groups include amino substituted groups such as glutamyl, aspartyl and asparaginyl, hydroxy substituted groups derived from glyceric acid, glycerol and pentaerythritol, and groups substituted with both hydroxy and amino such as threonyl.

Preferably linking group Y is selected from $C_{1-7}$ alkylene, alkenylene, —$(CH_2CH_2$—O$)_p$—, —$(CH_2CH_2CH_2$—O$)_p$—, 5 or 6 membered cycloalkylene or heterocyclyl, $C_{1-7}$ alkenedioyl, $C_{1-7}$ alkanedioyl, $C_{1-7}$ alkylenedioxy, $C_{1-7}$ alkylenedicarbonyl and groups of the formula —$(R^1)_m$—$R^2$—$(R^3)_n$—, optionally substituted with one or two substituents selected from $C_{1-5}$ alkyl, hydroxy, halo, amino, $C_{1-5}$ alkyloxy and nitro; where $R^1$ and $R^3$ are selected from $C_{1-5}$ alkylene, 5 or 6 membered cycloalkylene or heterocyclyl, —$(CH_2CH_2$—O$)_p$—, —$(CH_2CH_2CH_2$—O$)_p$—, $R^2$ is selected from —O—, —S—, —S—S—, —NR—, —NRC(O)O—, —NRC(O)NR—, alkylenedioxyl, and —C(O)—, p is 1 to 8 and m, n and R are as defined above.

More preferably the linking group is selected from $C_{1-5}$ alkylene, $C_{1-5}$ alkenylene, —$(CH_2CH_2$—O$)_p$—, $C_{1-5}$ alkanedioyl, $C_{1-5}$ alkylenedicarbonyl, —$(C_{1-5}$ alkylene$)_m$—$R^2$—$(C_{1-5}$ alkylene$)_n$—, —$(CH_2CH_2O)_m$—$R^2$—$(CH_2CH_2O)_n$—, optionally substituted with one or more substituents selected from $C_{1-3}$ alkyl, hydroxy, halo, $C_{1-3}$ alkyloxy; where $R^2$ is selected from —O—, —S—S—, —NR— and NRC(O)NR—, where R is H or $CH_3$, p is 1 to 4 and m and n are as defined above.

Most preferably the linking group Y is selected from —$CH_2$—, —$CH_2$—$CH_2$—, —$CH_2$—O—$CH_2$—, —CHOHCHOH—, —$CH_2$—S—S—$CH_2$— and —$(CH_2)_2$NHC(O)NH$(CH_2)_2$—.

The crosslinking agents according to the present invention may be prepared by conventional methods. In one such method an appropriate substrate, i.e. a diamine, dialcohol, dithiol, aminoalcohol, thiolalcohol or thiolamine, is reacted with an equimolar amount of a reactive acryloyl or methacryloyl species, such as acryloyl chloride or methacryloyl chloride, in a suitable solvent such as chloroform or tetrahydrofuran, to form a monoacryloyl (or monomethacryloyl) intermediate. This intermediate may be isolated and purified before further reaction with an equivalent amount of the other reactive acryloyl or methacryloyl species, or the complete reaction may be carried out in two steps in a single pot. Reaction with the acryloyl species may be followed by reaction with the methacryloyl species or vice versa.

Where there is little or no reactivity differential between the reactive ends of the substrate, eg. for diamines, dialcohols and dithiols, it may be desirable to first protect one end of the substrate with an appropriate protecting group such as t-BOC. The other end can then be reacted with the reactive acryloyl or methacryloyl species to form a monoacryloyl (or monomethacryloyl) intermediate. Removal of the protecting group is then followed by reaction with the other reactive methacryloyl or acryloyl species. It is also possible to achieve reaction predominantly at one end of such a substrate by controlling the pH of the reaction mixture.

Some of the monoacryloyl and monomethacryloyl intermediates are novel compounds and represent a further aspect of the invention.

Preferred crosslinking agents useful in the present invention include the following:

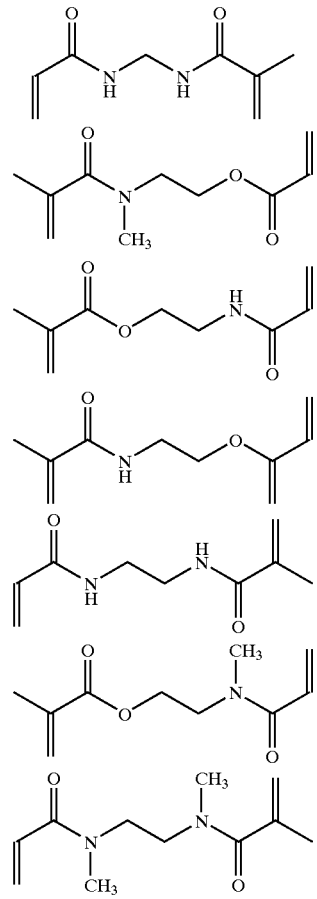

-continued

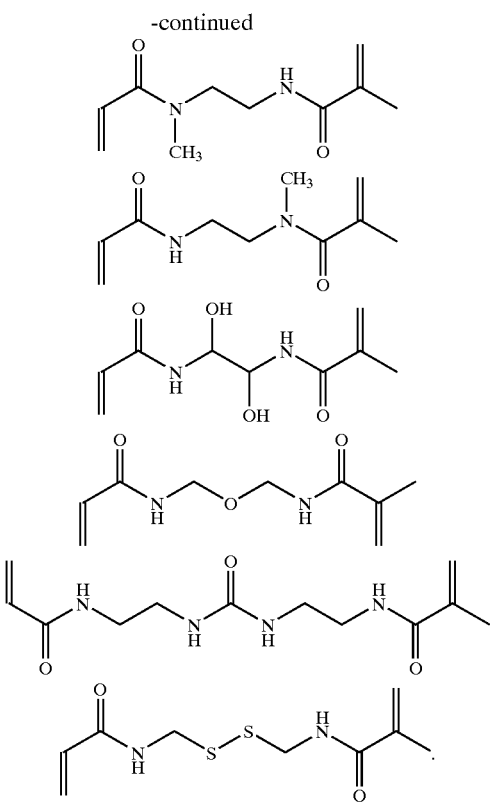

While not wishing to be limited by theory it is believed that the more reactive vinyl group will be preferentially incorporated into the polymer chain, for example the methacryloyl end of the crosslinking agent reacts first with the monomer to yield a polymer with pendant acryloyl units. In this way long linear chains of the monomer incorporating primarily methacryloyl groups of the crosslinking agent would be produced first, before crosslinking of the linear polymeric chains starts to occur. It is believed that this delayed crosslinking produces a gel having a microporous structure more suitable for the separation of biomolecules than known gels prepared from symmetrical crosslinking agents such as BIS.

Some of the bisamide, bithioester and amidethioester crosslinking agents according to the present invention are novel and accordingly in another aspect the invention there is provided a compound of formula:

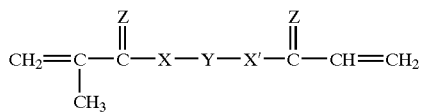

wherein X and X' are selected from —S— and —NR—, where R is H, alkyl or cycloalkyl, and Y and Z are as defined above, provided that when X and X' are both —NR—, Y is not —CH$_2$— and does not include a quarternary ammonium group.

Some of the amide-ester and thioester ester crosslinking agents of the present invention are also novel and, accordingly, in another aspect of the invention there is provided a compound of formula:

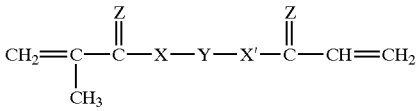

where one of X and X' is —O— and the other is selected from —S— and —NR—, where R is H, alkyl or cycloalkyl, and Y and Z are as defined above; provided that Y is not $C_{1-5}$ alkylene and does not include a quarternary ammonium group, and that when the other of X and X' is —NH—, Y is not methyleneoxy-2-hydroxypropylene.

In addition to being useful crosslinking agents in the preparation of crosslinked polymer gel, the novel compounds, in view of their ability to form cross linked polymer networks, may be used as precursors for novel polymeric materials, or they may be used in admixtures with other polymerisable entities to produce novel crosslinked polymeric compounds to form products such as optical lenses, dental cements, surface coatings, plastic films, heat resistant plastics and adhesives. These compounds also have potential as biologically active compounds (e.g. antitumour agents).

The gels of the present invention may be prepared by conventional methods. They may be prepared in a variety of polymer concentrations, depending on the sizes of the molecules to be separated. Polyacrylamide gels crosslinked with BIS are commonly used to separate DNA fragments less than 1 kb in length. For this purpose the gels are prepared having acrylamide concentrations in the range of about 3.5 to 20%. Gels having a concentration of 3.5% are useful for separating DNA fragments of about 100 to 1000 nucleotides while gels having an acrylamide concentration of about 20% are useful for separating fragments having from about 10 to 100 nucleotides.

Since the microporous structure of the gels according to the present invention is dependent on the particular crosslinking agent used, as well as the monomer concentration, the optimum monomer concentration for a particular biomolecule size range may differ somewhat from the optimum monomer concentrations known for acrylamide/BIS systems. The optimum concentration can be readily determined from standard trial runs.

Generally, however, the crosslinking agent can be employed in an amount of approximately 1 to 30 wt. %, preferably 2 to 10 wt. %, based on the total weight of the monomer and the crosslinking agent (% C). For the total gel concentration, monomers may be employed in approximately 1 to 50 wt %, preferably 1.5 to 20 wt %, based on total solution volume (% T).

The crosslinking polymerization reaction by which the novel gels of this invention are prepared is generally carried out in an aqueous medium and can be initiated by known initiators or polymerization catalysts. Suitable free radical-providing initiator systems are benzoyl peroxide, t-butylhydroperoxide, lauroyl peroxide, cumene hydroperoxide, tetralin peroxide, acetyl peroxide, caproyl peroxide, t-butylperbenzoate, t-butyldiperphthalate, methylethylketone peroxide, hydrogen peroxide-$Fe^{2+}$-ascorbic acid, riboflavin-light, methylene blue-light, and various persulfate salts in conjunction with N,N,N',N'-tetramethylethylenediamine (TEMED), diethylmethylaminediamine (DEMED), 3-dimethylaminopropionitrile (DMAPN) or similar reagents and ammonium persulfate-metabisulfite. Another class of free radical generating initiators are azocompounds such as azodiiosobutyronitrile, azodiisobutyramide, azobis (dimethylvaleronitrile), azobis (methylbutyronitrile), dimethyl, diethyl, or dibutylazobism-ethylvalerate. These and similar reagents contain a N,N double bond attached to aliphatic carbon atoms, at least one of which is tertiary. The amount and type of initiator is generally indicated by the nature and concentrations of the monomer and crosslinking agent used. The optimum amount of initiator is also affected by the presence of any accompanying impurities. Generally speaking, however, the initiator can be employed in the amount of approximately 0.3 to 5 wt. % based on the total amount of the monomer and crosslinking agent. The preferred initiator system is TEMED, DEMED or DMAPN and a persulfate salt.

Methods known in the art for utilizing polyacrylamide gels for determination of nucleotide sequences usually involve the preparation of the gels in given thicknesses, such as between glass plates, or plates of synthetic transparent material, to a thickness of approximately 3 mm. The gel may also be polymerized onto a support film. DNA samples labelled such as with $^{32}P$, $^{35}S$ or fluorescent dyes are placed onto sample slots and electrophoresed. After electrophoresis (which generally occurs over a period of from 1 hour to a number of days) the gel is removed from the plates and autoradiography performed. In automated systems, fluorescent labelled nucleotides are monitored during the separation. Autoradiography requires 10 to 20 hours after which time films are studied to determine nucleotide sequence. The preparation of gels for autoradiography of $^{35}S$ nucleotides requires immersion in 10% acetic acid to remove urea and handling of the gels with caution due to extreme fragility.

When proteins are to be separated by electrophoretic methods based on their size, an ionic detergent, such as sodium dodecyl sulfate (SDS) is generally added to the polyacrylamide gel, optionally in conjunction with other denaturants, to unfold the protein and provide a net negative charge. It is then possible to estimate molecular sizes from mobilities compared to known standards. In native electrophoresis where separation is made according to change and/or molecular weight, the polyacrylamide gels are generally used in combination with acidic, basic or neutral buffer systems in the absence of denaturing agents. Electrodes are positioned according to the predicted net charge of the sample at the pH used.

The gels according to the present invention may include conventional additives known to the art as required by the technique employed. These additives include detergents, such as SDS; denaturing agents, such as urea, N,N'-dimethylformamide, n-propylalcohol, formamide, dimethyl formamide and glycine; high molecular weight polymers, such as polyvinyl alcohol, linear polyacrylamide, polyethylene glycols; and low molecular weight species such as glycerol and sucrose. The gels may also include a suitable buffer system.

A number of suitable buffer systems are disclosed in WO91/14489 the disclosure of which is incorporated herein by reference. These are shown below in Table I.

TABLE 1

| Buffer | pH |
| --- | --- |
| Citrate-phosphate | 3.2 |
| Succinate | 5.2 |
| Phosphate-magnesium sulfate | 6.8 |
| Tris-EDTA-acetate | 7.2 |
| Tris-HCl-magnesium sulfate | 7.4 |
| Tris-EDTA-acetate | 7.8 |
| Tris-magnesium chloride | 8.0 |

TABLE 1-continued

| Buffer | pH |
| --- | --- |
| Tris-EDTA-borate | 8.3 |
| Tris-EDTA-borate | 8.6 |
| Tris-EDTA-lactate | 8.6 |
| Tris-veronal | 8.6 |
| Veronal | 9.2 |
| Tris-EDTA-borate | 9.5 |
| Tris-EDTA-phosphate | 8.6 |
| Tris-glycine | 8.8 |
| Tris-glycine-SDS | 8.8 |
| Sodium phosphate | 7.5 |
| Sodium-phosphate SDS | 7.5 |
| Ethanolamine/GABA* | 9.5–10 |
| Tris/acetate/GABA | 9.6–10.2 |
| Ammediol/GABA | 9.6–10.2 |
| Ammediol/HCl | 9.6–10.2 |
| Tris-HCl | 9.3–9.6 |

*GABA = gamma, amino butyric acid

In addition to the analytical and preparative separation of biomolecules, the gels according to the present invention may be used to estimate molecular weights, and elucidate composition of complex mixtures. The gels may also be used in the sequencing of proteins and DNA, as polyelectrolytes, and may find use in environmental and quality control applications.

The performance of known gels has so far been limited by a number of factors including (a) restriction on pore size range available (thereby restricting the molecular weight range of fragments which can be separated), (b) the susceptibility of some gels to hydrolysis in slightly alkaline media, or to premature mechanical degradation and (c) high background staining caused by the amide linkages of BIS. An advantage of the present invention is the ability to control or modify gel formation to produce a gel having the desired characteristics (e.g. pore size, mechanical stability, alkaline stability, background staining etc.) by selecting an appropriate asymmetrical crosslinking agent.

In order to more clearly describe the invention reference will be made to the following examples and drawings which describe some preferred embodiments of the invention. However the particularity of the examples and drawings is not to be understood to supersede the generality of the preceding description.

BRIEF DESCRIPTION OF DRAWINGS

Referring to the drawings.

EXAMPLES

Example 1

Preparation of 2-Methacrylethylacrylamide

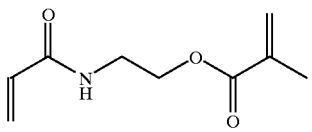

Figure 1:
FIG. 1 shows the separation of a standard protein mixture achieved using gels according to the present invention (Gels B, C and D) compared to a standard BIS gel (Gel A), where the concentrations of acrylamide and crosslinking agent are equivalent, on a mole:mole basis. with a 10% T 3% C BIS gel.
Figure 1:
Figure 1:
Figure 1:

Acryloyl chloride (25 mmol, 2.0 cm³) in chloroform (25 cm³) was added dropwise to a stirred solution of ethanolamine (50 mmol, 3.0 cm³) in chloroform (50 cm³) at 0° C. After the addition was complete, the reaction mixture was stirred at 0° C. for a further 2 h. The monohydrochloride precipitate was removed by filtration and the filtrate evaporated under reduced pressure to give the crude product as a yellow oil. This was then taken up in a slurry of basic alumina in chloroform, and stirred at room temperature for 18 h. Removal of the alumina and concentration of the solution then gave the desired (2-hydroxy)ethylacrylamide as a clear colorless oil. (2.5 g, 87%). $\delta_H$ (400 MHz; CDCl$_3$) 7.06 (1H, br s), N$\underline{H}$; 6.24 (1H, dd, J 17.0, 1.8 Hz), HC=C$\underline{H}_a$H$_b$; 6.17 (1H, dd, J 17.0, 9.8 Hz), $\underline{H}$C=CH$_a$$\underline{H}_b$; 5.62 (1H, dd, J 9.9, 1.8 Hz), HC=CH$_a$$\underline{H}_b$; 4.13 (1H, s), O$\underline{H}$; 3.69 (2H, t, J 5.1 Hz), C$\underline{H}_2$OH; 3.43 (2H, td, J 5.6, 4.9 Hz), NHC$\underline{H}_2$, $\delta_C$ (75.4 MHZ; CDCl$_3$) 166.76, $\underline{C}$=O; 130.50, H$\underline{C}$=CH$_2$; 126.81, HC=$\underline{C}$H$_2$; 61.70, $\underline{C}$H$_2$OH; 42.41, NH$\underline{C}$H$_2$, Found: M$^+$. 115.14.

To a stirred solution of N-(2-hydroxyethyl)acrylamide (7.0 mmol, 0.8 g) and triethylamine (7.7 mmol, 1.1 cm³) in chloroform (30 cm³) at room temperature, was added dropwise, a solution of methacryloyl chloride (7.7 mmol, 0.8 cm³) in chloroform (15 cm³) under an atmosphere of nitrogen. After the addition was complete, the reaction mixture was stirred for 16 h. The reaction mixture was then washed with 2M HCl, and the organic fractions collected, dried and concentrated under reduced pressure to give the crude product as a yellow oil. This was then taken up in a slurry of basic alumina in chloroform and stirred at room temperature for 18 hr. Removal of the alumina and concentration of the filtrate gave a yellow oil which was subjected to flash chromatography (silica gel, diethyl ether:hexane:methanol elution) to afford 2-methacrylethylacrylamide (R$_f$ 0.51) as a clear yellow oil (0.77 g, 61%). $\delta_H$ (400 MHz; CDCl$_3$) 6.20 (1H, br m), N$\underline{H}$; 6.26 (1H, dd, J 17.0, 1.5 Hz), RHNOCCH=C$\underline{H}_c$H$_d$; 6.11 (1H, dd, J 17.0, 10.3 Hz), RHNOCC$\underline{H}$=CH$_c$H$_d$; 6.10 (1H, br s), ROO(H$_3$C)C=C$\underline{H}_a$H$_b$; 5.63 (1H, dd, J 10.3, 1.5 Hz), RHNOCCH=CH$_a$$\underline{H}_b$; 5.58 (1H, m), ROO(H$_3$C)C=CH$_a$$\underline{H}_b$; 4.26 (2H, t, J 5.4 Hz), C$\underline{H}_2$OC=O; 3.63 (2H, td, J 5.6, 5.4 Hz), C$\underline{H}_2$NHC=O; 1.92 (3H, S) C$\underline{H}_3$. $\delta_C$ (75.4 MHZ; CDCl$_3$) 167.48, O$\underline{C}$=O; 165.69, HN$\underline{C}$=O; 135.86, ROO(H$_3$C)$\underline{C}$=CH2; 130.56, RHNOC$\underline{C}$H=CH$_2$; 126.67, RHNOCCH=$\underline{C}$H$_2$; 126.13, ROO(H$_3$C)C=$\underline{C}$H$_2$; 63.32, $\underline{C}$H$_2$OC=O; 38.89, $\underline{C}$H$_2$NHC=O; 18.23, $\underline{C}$H$_3$. Found: M$^+$. 183.22.

Example 2

Preparation of 2-Acrylethylmethacrylamide

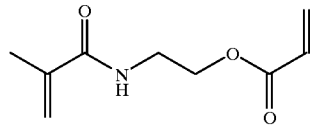

Methacryloyl chloride (25 mmol, 2.4 cm³) in chloroform (25 cm³) was added dropwise to a stirred solution of ethanolamine (50 mmol, 3.0 cm³) in chloroform (50 cm³) at 0/C. After the addition was complete, the reaction mixture was stirred at 0/C for a further 2 h. The monohydrochloride precipitate was removed by filtration and the filtrate evaporated under reduced pressure to give the crude product as a yellow oil. This was then taken up in a slurry of basic alumina in chloroform, and stirred at room temperature for 18 h. Removal of the alumina and concentration of the solution then gave the (2-hydroxy)-ethylmethacrylamide product as a clear colorless oil. (3.2 g. 96%). $\delta_H$ (400 MHz: CDCl$_3$) 6.57 (1H, br m), N$\underline{H}$; 6.27 (1H, dd, J 17.0, 1.5 Hz), HC=C$\underline{H}_a$H$_b$; 6.14 (1H, dd, J 17.0, 10.0 Hz), $\underline{H}$C=CH$_a$H$_b$; 5.65 (1H, dd, J 10.0, 1.5 Hz), HC=CH$_a$$\underline{H}_b$; 3.74 (2H, t, J 4.9 Hz), C$\underline{H}_2$OH; 3.48 (2H, td, J 5.6, 4.9 Hz), NHC$\underline{H}_2$; 3.37 (1H, s), O$\underline{H}$. $\delta_C$ (75.4 MHZ; CDCl$_3$) 166.76, $\underline{C}$=O; 130.50, H$\underline{C}$=CH$_2$; 126.81, HC=$\underline{C}$H$_2$; 61.70, $\underline{C}$H$_2$OH; 42.41, NH$\underline{C}$H$_2$. Found: M$^+$. 129.17.

To a stirred solution of N-(2-hydroxyethyl)methacrylamide (10 mmol, 1.3 g) and triethylamine (11 mmol, 1.5 cm³) in chloroform (40 cm³), was added dropwise, a solution of acryloyl chloride (11 mmol, 0.9 cm³) in chloroform (20 cm³) at room temperature under a nitrogen atmosphere. After the addition was complete, the reaction mixture was stirred for a further 16 h. The usual work-up as for example 1 then gave the crosslinking monomer, 2-acrylethylmethacrylamide (R$_f$ 0.54) as a clear, colorless oil (0.6 g, 32%). $\delta_H$ (400 MHz; CDCl$_3$) 6.45 (1H, br m). N$\underline{H}$; 6.38 (1H, dd, J 17.8, 2.0 Hz), ROOCH=C$\underline{H}_a$H$_b$; 6.08 (1H, dd, J 17.8, 8.9 Hz), ROOC$\underline{H}$=CH$_a$H$_b$; 5.82 (1H, dd, J 8.9, 2.0 Hz), ROOCH=CH$_a$$\underline{H}_b$;5.66 (1H, s), RHNOC(H$_3$C)C=C$\underline{H}_c$H$_d$; 5.29 (1H, s), RHNOC(H$_3$C)C=CH$_c$$\underline{H}_d$; 4.25 (2H, t, J 4.9 Hz), C$\underline{H}_2$OCO; 3.57 (2H, td, J 4.9, 4.7 Hz), C$\underline{H}$NHCO; 1.94 (3H, s), C$\underline{H}_3$. $\delta_C$(75.4 MHZ; CDCl$_3$) 168.52, HN$\underline{C}$=O; 166.22, O$\underline{C}$=O; 139.60, RHNOC(H$_3$C)$\underline{C}$=CH$_2$; 131.34, ROOCH=$\underline{C}$H$_2$; 127.83, ROO$\underline{C}$H=CH$_2$; 119.69, RHNOC(H$_3$C)C=$\underline{C}$H$_2$; 63.07, $\underline{C}$H$_2$OC=O; 38.97, $\underline{C}$H$_2$NHC=O; 18.43, $\underline{C}$H$_3$. Found: M$^+$. 183.22.

Example 3

Preparation of N-Methyl, N-acryloyl-2-ethylmethacrylate

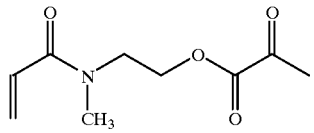

Acryloyl chloride (25 mmol, 2.0 cm³) in chloroform (25 cm³) was added dropwise to a stirred solution of 2-(methylamino)ethanol (50 mmol, 4.0 cm³) in chloroform (50 cm³) at 0° C. After the addition was complete, the reaction mixture was stirred at 0° C. for a further 2 h. The monohydrochloride precipitate was removed by filtration and the filtrate evaporated under reduced pressure to give the crude product as a yellow oil. This was then taken up in a slurry of basic alumina in chloroform, and stirred at room temperature for 18 h. Removal of the alumina and concentration of the solution then gave the desired N-methyl, N-acryloyl-2-ethanol as a clear colorless oil (2.77 g. 86%). $\delta_H$ (300 MHz; CDCl$_3$) 6.47 (1H, dd, J 17.0, 1.8 Hz), HC=C$\underline{H}_a$H$_b$; 6.23 (1H, dd, J 17.0. 9.9 Hz), $\underline{H}$C=CH$_a$H$_b$; 5.57 (1H, dd, J 10.0, 1.9 Hz), HC=CH$_a\underline{H}_b$; 4.07 (1H, s), O$\underline{H}$; 3.77 (2H, t, J 5.1 Hz), C$\underline{H}$hd 2OH; 3.46 (2H, td, J 5.6. 4.9 Hz), NC$\underline{H}_2$, 3.10 (3H, br m), N(CH$_3$). $\delta_C$ (75.4 MHZ; CDCl$_3$) 166.85, $\underline{C}$=O; 130.53, H$\underline{C}$=CH$_2$; 126.85, HC=$\underline{C}$H$_2$; 60.88, $\underline{C}$H$_2$OH; 43.76, N$\underline{C}$H$_2$. Found: M$^+$. 129.17.

To a stirred solution of intermediate (7.0 mmol, 0.8 g) and triethylamine (7.7 mmol, 1.1 cm$^3$) in chloroform (30 cm$^3$) at room temperature, was added dropwise, a solution of methacryloyl chloride (7.7 mmol, 0.8 cm$^3$) in chloroform (15 cm$^3$) under an atmosphere of nitrogen. The workup as for example 1 then afforded N-methyl, N-acryloyl-2-ethylmethacrylate as a clear yellow oil (0.65 g, 47%). $\delta_H$ (400 MHz; CDCl$_3$) 6.54 (1H, dd, J 17.8, 10.3 Hz), N(CH$_3$)C$\underline{H}$=CH$_a$H$_b$; 6.33 (1H, dd, J 17.8, 2.0 Hz), N(CH$_3$)CH=C$\underline{H}_a$H$_b$; 6.15 (1H, br m), O$_2$C(H$_3$C)C=C$\underline{H}_c$H$_d$;5.90 (1H, br m), O$_2$C(H$_3$C)C=CH$_c\underline{H}_d$; 5.63(1H, dd, J 10.1, 2.0 Hz), N(CH$_3$)CH=CH$_a\underline{H}_b$; 4.09 (2H, t, J 4.9 Hz), C$\underline{H}_2$OCO; 3.48 (2H, td, J 4.9, 4.7 Hz), C$\underline{H}_2$N(CH$_3$)CO; 3.03 (3H, s), N(C$\underline{H}_3$); 1.88 (3H, s), C$\underline{H}_3$. $\delta_C$ (75.4 MHZ; CDCl$_3$) 167.50, O$\underline{C}$=O; 166.85, N(CH$_3$)$\underline{C}$=O; 136.46, RO$_2$C(H$_3$C)$\underline{C}$=CH$_2$; 130.92, RN(CH$_3$)OCH=$\underline{C}$H$_2$; 126.79, RN(CH$_3$)O$\underline{C}$H=CH$_2$; 124.10, RO$_2$C(H$_3$C)C=$\underline{C}$H$_2$; 61.75, $\underline{C}$H$_2$OC=O; 45.33, $\underline{C}$H$_2$N(CH$_3$)C=O; 35.61, N($\underline{C}$H$_3$); 17.20, $\underline{C}$H$_3$. Found: M$^+$. 197.25.

Example 4

Preparation of N-Methyl, N-methacryloyl-2-ethylacrylate

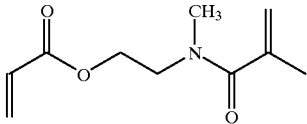

Methacryloyl chloride (25 mmol. 2.4 cm$^3$) in chloroform (25 cm$^3$) was added dropwise to a stirred solution of 2-(methylamino)ethanol (50 mmol, 4.0 cm$^3$) in chloroform (50 cm$^3$) at 0° C. After the addition was complete, the reaction mixture was stirred at 0° C. for a further 2 h. The monohydrochloride precipitate was removed by filtration and the filtrate evaporated under reduced pressure to give the crude product as a yellow oil. This was then taken up in a slurry of basic alumina in chloroform, and stirred at room temperature for 18 h. Removal of the alumina and concentration of the solution then gave the desired N-methyl, N-methacryloyl-2-ethanol intermediate as a clear colorless oil (3.22 g, 90%). $\delta_H$ (300 MHz; CDCl$_3$) 5.76 (1H, br m), N(H$_3$C)C=C$\underline{H}_a$H$_b$; 5.45 (1H, br m), N(H$_3$C)C=CH$_a\underline{H}_b$; 4.15 (1H, s), O$\underline{H}$; 3.82 (2H, t, J 5.1 Hz), C$\underline{H}_2$OH; 3.53 (2H, td, J 5.6, 4.9 Hz), NC$\underline{H}_2$, 3.14 (3H, br m), N(CH$_3$); 1.97 (3H, s), C$\underline{H}_3$. $\delta_C$ (75.4 MHZ; CDCl$_3$) 171.88, $\underline{C}$=O; 141.05, (H$_3$C)$\underline{C}$=CH$_2$; 126.81, (H$_3$C)C=$\underline{C}$H$_2$; 62.35, $\underline{C}$H$_2$OH; 43.21, N$\underline{C}$H$_2$.36.56, N(CH$_3$); 19.53, C$\underline{H}_3$. Found: M$^+$. 143.20.

To a stirred solution of intermediate (7.0 mmol, 0.8 g) and triethylamine (7.7 mmol, 1.1 cm$^3$) in chloroform (30 cm$^3$) at room temperature, was added dropwise, a solution of acryloyl chloride (7.7 mmol, 0.6 cm$^3$) in chloroform (15 cm$^3$) under an atmosphere of nitrogen. The work-up as for example 1 then yielded N-methyl, N-acryloyl-2-ethylmethacrylate as a clear yellow oil (0.72 g, 52%). $\delta_H$ (400 MHz: CDCl$_3$) 6.38 (1H, dd, J 17.0, 1.5 Hz), O$_2$CCH=C$\underline{H}_c$H$_d$; 6.11 (1H, dd, J 17.0, 10.3 Hz), O$_2$CC$\underline{H}$=CH$_c$H$_d$; 5.77 (1H, dd, J 10.3, 1.5 Hz), O$_2$CCH=CH$_c\underline{H}_d$; 5,72 (1H, br m), N(H$_3$C)C=C$\underline{H}_a$H$_b$; 5.38 (1H, br m), N(H$_3$C)C=CH$_a\underline{H}_b$; 4.10 (2H, t, J 5.4 Hz), C$\underline{H}_2$OC=O; 3.47 (2H, td, J 5.6, 5.4 Hz), C$\underline{H}_2$N(CH$_3$)C=O; 3.04 (3H, s), N(CH$_3$); 1.95, (3H, s) C$\underline{H}_3$. $\delta_C$ (75.4 MHZ; CDCl$_3$) 172.80, N(H$_3$C)$\underline{C}$=O; 166.70, O$\underline{C}$=O; 140.16, N(H$_3$C)$\underline{C}$=CH$_2$; 131.85, RO$_2$CCH=$\underline{C}$H$_2$; 128.80, RO$_2$C$\underline{C}$H=CH$_2$; 126.67, N(H$_3$C)$\underline{C}$H=CH$_2$; 1119.56, N(H$_3$C)C=$\underline{C}$H$_2$; 61.60, $\underline{C}$H$_2$OC=O; 45.47, $\underline{C}$H$_2$N(CH$_3$)C=O; 36.35, N(CH$_3$); 19.24, $\underline{C}$H$_3$. Found: M$^+$. 197.25.

Example 5

Preparation of N-Methyl, N-methacryloyl, N'-acryloyl-ethylenediamine

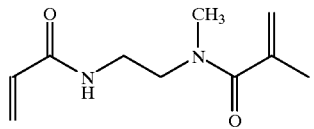

To a stirred solution of N-methyl-ethylenediamine (0.10 mol. 8.8 cm$^3$) in dioxane (50 cm$^3$), at room temperature and under a nitrogen atmosphere, was added a solution of S-tert-butyloxycarbonyl-4,6-dimethyl-2-mercaptopyrimidine (0.05 mol, 12 g) in dioxane (50 cm$^3$), dropwise, over 3 h. After the addition was complete, the solution was stirred at room temperature for a further 15 h. The precipitate which formed (4,6dimethyl-2-mercaptopyrimidine) was removed from the solution, and the filtrate conc. in vacuo to half its original volume (50 cm$^3$). To this residue, was added water (80 cm$^3$) and the solution then left to stand at room temperature for 15 min. The bis-(t-BOC)-diamine precipitate was then removed, and the filtrate conc. in vacuo. To the residue was added water (80 cm$^3$), and the solution subsequently saturated with sodium chloride. This saturated solution was extracted with ethyl acetate (4×40 cm$^3$), and the organic extracts combined, dried (MgSO$_4$), filtered, and conc. in vacuo to give an oil. This oil was dissolved in water (50 cm$^3$) and acidified to pH 3 with 1M hydrochloric acid. The solution was then extracted with ethyl acetate (3×100 cm$^3$). The aqueous layer was then collected, decolourized with activated charcoal and filtered over Celite. The filtrate was then conc. in vacuo. If necessary, fractional recystallization from room temperature methanol was used to separate the required product from any diamine dihydrochloride by-product. The filtrate was then conc. in vacuo. The product was isolated by trituration from hexane, to give a fine off-white solid which consisted of a mixture of N-t-BOC, N-methylethylenediamine monohydrochloride and N-t-BOC, N'-methyl ethylenediamine monohydrochloride in a 4:1 ratio (4.8 g, 45%), m.p. 104–105° C. $\delta_H$ (400 MHZ; methanol-d$_4$) 3.52–3.37 (2H, t, J 4.8 Hz), C$\underline{H}_2$NH; 3.31 (2H, t, J 4.8 Hz), C$\underline{H}_2$NH(CH$_3$); 2.81 (3H, s), NC$\underline{H}_3$; 1.43 (9H, s) C(C$\underline{H}_3$)$_3$. $\delta_C$ (75.4 MHz: methanol-d$_4$) 157.88, $\underline{C}$=O; 81.60 $\underline{C}$(CH$_3$)$_3$; 47.47, $\underline{C}$H$_2$NH(CH$_3$); 39.09, $\underline{C}$H$_2$NH; 28.65, C($\underline{C}$H$_3$)$_3$. Found: M$^+$. 210.72.

The intermediate N-t-BOC, N-methyl-ethylenediamine monohydrochloride (10.0 mmol, 2.11 g) was stirred with 2M NaOH (11 cm$^3$) at room temperature for 10 min. The solution was then cooled to 0° C., and to this, was added a solution of acryloyl chloride (11.0 mmol, 0.9 cm$^3$) in chloroform (30 cm$^3$), dropwise. After the addition was complete, the reaction mixture was stirred at 0° C. for a further 1 h. The organic and aqueous phases were then separated, and the aqueous phase extracted with chloroform. The organic extracts were combined, dried (MgSO4), filtered and conc. in vacuo, to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) afforded the major isomer N-t-BOC, N-methyl, N'-acryloyl-ethylenediamine ($R_f$ 0.27) as a pale yellow oil which solidified upon standing. Trituration from hexane then gave the product as a white solid (1.55 g, 68%). m.p. 56–57/C. $\delta_H$ (400 MHz; CDCl$_3$) 6.72 (1H, br s), NH: 6.20 (1H, d, J 17.3 Hz). CH=CH$_a$H$_b$; 6.05 (1H, dd, J 17.1. 10.3 Hz), CH=CH$_a$H$_b$; 5.58 (1H, d, J 10.0 Hz), CH=CH$_a$H$_b$; 3.43 (4H, m), 2×CH$_2$; 2.86 (3H, s), N(CH$_3$); 1.42 (9H, s), C(CH$_3$)$_3$. $\delta_C$ (100 MHZ; CDCl$_3$, 50/C) 165.90, NHO CCH=CH$_2$; 156.88. NCO$_2$C(CH$_3$)$_3$; 131.11, CH=CH$_2$; 125.56. CH=CH$_2$; 79.87 C(CH$_3$)$_3$; 47.62, CH$_2$NHCO$_2$C(CH$_3$)$_3$; 38.57, CH$_2$N(CH$_3$)OCCH=CH$_2$; 34.62, N(CH$_3$); 28.31, C(CH$_3$)$_3$. Found: M$^+$. 228.31.

N-t-BOC, N-methyl, N'-acryloyl-ethylenediamine (2.5 mmol, 0.57 g) was stirred in a solution of 3M HCl in ethyl acetate (2.5 cm$^3$) at room temperature for 30 min. The solution was then conc. in vacuo to give the intermediate N-methyl, N'-acryloyl-ethylenediamine monohydrochloride as a clear yellow oil. This intermediate (2.5 mmol) was then stirred at room temperature in 2M NaOH (3 cm$^3$) for 10 min. This reaction mixture was cooled to 0° C., and to this, was added a solution of methacryloyl chloride (2.8 mmol, 0.27 cm$^3$) in chloroform (7 cm$^3$), dropwise, over 30 min. After the addition was complete, the reaction mixture was stirred at 0° C. for a further 1 h. The organic and aqueous phases were then separated, and the aqueous phase extracted with chloroform. The organic extracts were combined, dried (MgSO$_4$), filtered and conc. in vacuo, to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) afforded N-t-BOC, N-methyl, N'-methacryloyl-ethylenediamine as a pale yellow oil (0.24 g, 48%). $\delta_H$ (300 MHz; CDCl$_3$) 6.79 (1H, br s), NH; 6.2 (1H, d, J 17.1 Hz), HC=CH$_a$H$_b$; 6.08 (1H, dd, J 17.1, 10.0), HC=CH$_a$H$_b$; 5.59 (1H, d, J 10.0 Hz), HC=CH$_a$H$_b$; 5.18 (br m), (H$_3$C)C=CH$_c$H$_d$; 5.00 (br m), (H$_3$C)C=CH$_c$H$_d$; 3.58 (4H, br m), 2×CH$_2$; 3.05, (3H, br m) N(CH$_3$); 1.90 (3H, br m), CH$_3$. $\delta_C$ (75.4 MHz; CDCl$_3$) 170.92. NOC(H$_3$C)C=CH$_2$; 162.87, NHOCHC=CH$_2$; 139.39, (H$_3$C)C=CH$_2$; 132.00, HC=CH$_2$; 125.42, H C=CH$_2$; 119.56, (H$_3$C)C=CH$_2$; 44.97, CH$_2$CH$_2$; 36.21, CH$_2$CH$_2$; 33.98, N(CH$_3$); 19.24, CH$_3$. Found: M$^+$. 196.26

Example 6

Preparation of N-Methyl, N-acryloyl, N'-methacryloyl-ethylenediamine

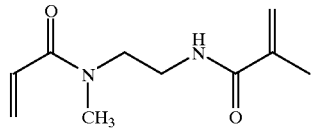

The intermediate N-t-BOC, N-methyl-ethylenediamine monohydrochloride prepared in example 5 (10 mmol, 2.1 g) was stirred with 2M NaOH (11 cm$^3$) at room temperature for 10 min. The solution was then cooled to 0° C., and to this, was added a solution of methacryloyl chloride (11 mmol, 1.1 cm$^3$) in chloroform (30 cm$^3$), dropwise. After the addition was complete, the reaction mixture was stirred at 0° C. for a further 1 h. The organic and aqueous phases were then separated, and the aqueous phase extracted with chloroform. The organic extracts were combined, dried (MgSO$_4$), filtered and conc. in vacuo, to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) afforded N-t-BOC, N-methyl, N'-methacryloyl-ethylenediamine ($R_f$ 0.51) as a yellow oil (1.63 g, 67%). $\delta_H$ (400 MHz; CDCl$_3$) 6.94 (1H, br s), HNOC(H$_3$C)C=CH$_a$H$_b$; 5.74 (1H, br m), (H$_3$C)C=C H$_a$H$_b$; 5.30 (1H, br m), (H$_3$C)C=CH$_a$H$_b$; 3.43 (4H, br m). 2×CH$_2$; 2.87 (3H, s), N(CH$_3$); 1.93 (3H, br m), CH$_3$; 1.44 (9H, s), C(CH$_3$)$_3$. $\delta_C$ (75.4 MHz; CDCl$_3$) 168.52, NHO C(H$_3$C)C=CH$_2$; 157.33, NHCO$_2$C(CH$_3$)$_3$; 139.36, (H$_3$C) C=CH$_2$; 119.81, (H$_3$C)C=CH$_2$; 80.85 C(CH$_3$)$_3$; 47.32, CH$_2$N(CH$_3$)OC(H$_3$C)C=CH$_2$; 39.32, CH$_2$NHCO$_2$C(CH$_3$)$_3$; 34.68, N(CH$_3$); 28.33, C(CH$_3$)$_3$; 18.47, CH$_3$. Found: (MH$^+$) 243.17178.

N-t-BOC, N'-methyl, N'-methacryloyl-ethylenediamine (2.5 mmol, 0.61 g) was stirred in a solution of 3M HCl in ethyl acetate (2.5 cm$^3$) at room temperature for 30 min. The solution was then conc. in vacuo to give the intermediate N-methyl, N'-methacryloyl-ethylenediamine monohydrochloride as a clear yellow oil. This intermediate (2.5 mmol) was then stirred at room temperature in 2M NaOH (3 cm$^3$) for 10 min. The reaction mixture was cooled to 0° C. and to this, was then added a solution of acryloyl chloride (2.8 mmol, 0.23 cm$^3$) in chloroform (7 cm$^3$), dropwise, over 30 min. After the addition was complete, the reaction mixture was stirred at 0° C. for a further 1 h. The organic and aqueous phases were then separated, and the aqueous phase extracted with chloroform. The organic extracts were combined, dried (MgSO$_4$), filtered and conc. in vacuo, to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) then gave the crosslinker N-methyl, N-acryloyl, N'-methacryloyl-ethylenediamine as a pale yellow oil (0.26 g, 53%). $\delta_H$ (300 MHz; CDCl$_3$) 7.01 (1H, br s), NH; 6.50 (1H, dd, J 16.8, 10.4 Hz), HC=CH$_a$H$_b$; 6.22 (1H, dd, J 12.4, 2.0), HC=CH$_a$H$_b$; 5.66 (br m), (H$_3$C)C=CH$_c$H$_d$; 5.61 (1H, d, J 10.5 Hz), HC=CH$_a$H$_b$; 5.23 (br m) (H$_3$C)C=CH$_c$H$_d$; 3.57 (2H, br m), CH$_2$; 3.43 (2H, br m), CH$_2$; 3.00, (3H, br m) N(CH$_3$);1.85 (3H, br m), CH$_3$. $\delta_C$ (75.4 MHz; CDCl$_3$, 50° C.) 166.10, NHOC(H$_3$C)C=CH$_2$; 165.04, NO CHC=CH$_2$; 140.40, (H$_3$C)C=CH$_2$; 130.92, HC=CH$_2$; 126.01, HC=CH$_2$; 118.50, (H$_3$C)C=CH$_2$; 44.83, CH$_2$CH$_2$; 35.47, CH$_2$CH$_2$; 34.12, N(CH$_3$); 18.50, CH$_3$. Found: M$^+$. 196.26.

Example 7
Preparation of N-Acryloyl, N'-methacryloyl, N,N'-dimethyl-ethylenediamine

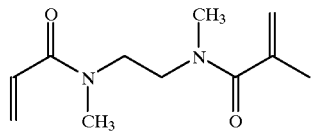

Method (a)

To a stirred solution of N,N'-dimethyl-ethylenediamine (0.10 mol, 12.4 cm$^3$) in dioxane (50 cm$^3$), at room temperature and under a nitrogen atmosphere, was added a solution of S-tert-butyloxycarbonyl-4,6-dimethyl-2-mercaptopyrimidine (0.05 mol, 12 g) in dioxane (50 cm$^3$), dropwise, over 3 h. After the addition was complete, the solution was stirred at room temperature for a further 15 h. The workup as in example 5 gave the product which was isolated by trituration from hexane, to give N-t-BOC, N,N'-dimethyl-ethylenediamine monohydrochloride as a white crystalline solid (4.99 g, 45%). m.p. 108–110° C. $\delta_H$ (400 MHz; methanol-d$_4$) 3.60 (2H, br m), CH$_2$N(CH$_3$); 3.20 (2H, t, J 6.25 Hz), CH$_2$NH(CH$_3$); 2.92 (3H, s), NCH$_3$; 2.75 (3H, s), HNCH$_3$; 1.47 (9H, s), C(CH$_3$)$_3$. $\delta_C$ (75.4 MHz; methanol-d$_4$) 157.83, C=O; 81.52 C(CH$_3$)$_3$; 48.43, NH(CH$_3$); 46.26, CH$_2$NH(CH$_3$); 35.32, CH$_2$NH(CH$_3$); 33.97, N CH$_3$; 28.68, C(CH$_3$)$_3$. Found: M$^+$. 224.75.

The intermediate N-t-BOC, N,N'-dimethyl-ethylenediamine monohydrochloride (5.0 mmol, 1.12 g) was stirred with 2M NaOH (11 cm$^3$) at room temperature for 10 min. The solution was then cooled to 0/C, and to this, was added a solution of acryloyl chloride (5.5 mmol, 0.45 cm$^3$) in chloroform (11 cm$^3$), dropwise, over 30 min. After the addition was complete, the reaction mixture was stirred at 0/C for a further 1 h. The organic and aqueous phases were then separated, and the aqueous phase extracted with chloroform. The organic extracts were combined, dried (MgSO4), filtered and conc. in vacuo, to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) afforded N-t-BOC, N'-acryloyl, N,N'-dimethyl-ethylenediamine as a yellow oil (0.62 g, 51%). $\delta_H$ (300 MHz; CDCl$_3$) 6.56 (1H, dd, J 16.8, 10.4 Hz), CH=CH$_a$H$_b$; 6.35 (1H, d, J 15.0 Hz), CH=CH$_a$H$_b$; 5.67 (1H, d, J 10.3 Hz), CH=CH$_a$H$_b$; 3.55 (2H, br m), CH$_2$; 3.37 (2H, m), CH$_2$; 3.07 (3H, m), N(CH$_3$); 2.86 (3H, m), N(CH$_3$); 1.45 (9H, m), C(CH$_3$)$_3$. $\delta_C$ (75.4 MHz; CDCl$_3$) 166.26, NOCHC=CH$_2$; 155.57, N CO$_2$C(CH$_3$)$_3$; 127.77, HC=CH$_2$; 126.89, HC=CH$_2$; 79.23, C(CH$_3$)$_3$; 47.77, CH$_2$N(CH$_3$)OCHC=CH$_2$; 46.82, CH$_2$N(CH$_3$)CO$_2$C(CH$_3$)$_3$; 35.87, CH$_2$N(CH$_3$)OCHC=CH$_2$; 34.54, CH$_2$N(CH$_3$)CO$_2$C(CH$_3$)$_3$; 28.22, C(CH$_3$)$_3$. Found: M$^+$. 242.34.

N-t-BOC, N'-acryloyl, N,N'-dimethyl-ethylenediamine (2.0 mmol, 0.46 g) was stirred in a solution of 3M HCl in ethyl acetate (2 cm$^3$) at room temperature for 30 min. The solution was then conc. in vacuo to give N'-acryloyl, N,N'-dimethyl-ethylenediamine monohydrochloride as a clear yellow oil. This intermediate was stirred at room temperature in 2M NaOH (3 cm$^3$) for 10 min. The reaction mixture was then cooled to 0° C., and to this, was then added a solution of methacryloyl chloride (2.2 mmol, 0.22 cm$^3$) in chloroform (5 cm$^3$) dropwise, over 30 min. After the addition was complete, the reaction mixture was stirred at 0° C. for a further 1 h. The organic and aqueous phases were then separated, and the aqueous phase extracted with chloroform. The organic extracts were combined, dried (MgSO$_4$), filtered and conc. in vacuo, to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) afforded N-acryloyl, N'-methacryloyl, N,N'-dimethyl-ethylenediamine as a yellow oil (0.12 g, 28%). $\delta_H$ (300 MHz; CDCl$_3$) 6.49 (1H, dd, J 16.8, 10.4 Hz), HC=CH$_a$H$_b$; 6.26 (1H, d, J 16.5), HC=C H$_a$H$_b$; 5.66 (1H, m), HC=CH$_a$H$_b$; 5.12 (1H, br m), (H$_3$C) C=CH$_c$H$_d$; 4.92 (1H, br m), (H$_3$C)C=CH$_c$H$_d$; 3.53 (4H, br m), 2×CH$_2$; 3.05 (3H, m) N(CH$_3$); 2.98 (3H, m) N(CH$_3$); 1.85 (3H, m), CH$_3$. $\delta_C$ (75.4 MHz; CDCl$_3$) 170.92, NO C(H$_3$C)C=CH$_2$; 165.04, NOCHC=CH$_2$; 139.39, (H$_3$C) C=CH$_2$; 130.92, HC=CH$_2$; 126.01, HC=CH$_2$; 119.56, (H$_3$C)C=CH$_2$; 43.23, CH$_2$CH$_2$; 43.09, CH$_2$CH$_2$; 36.21, N(CH$_3$); 35.47, N(CH$_3$); 19.24, CH$_3$. Found: M$^+$. 210.29.

Method (b)

The intermediate N-t-BOC, N,N'-dimethyl-ethylenediamine monohydrochloride (5.0 mmol, 1.12 g) as prepared above was stirred with 2M NaOH (11 cm$^3$) at room temperature for 10 min. The solution was then cooled to 0° C., and to this, was added a solution of methacryloyl chloride (5.5 mmol, 0.55 cm$^3$) in chloroform (11 cm$^3$), dropwise, over 30 min. After the addition was complete, the reaction mixture was stirred at 0° C. for a further 1 h. The organic and aqueous phases were then separated, and the aqueous phase extracted with chloroform. The organic extracts were combined, dried (MgSO$_4$), filtered and conc. in vacuo. to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) then afforded N-t-BOC, N'-methacryloyl, N,N'-dimethyl-ethylenediamine as a pale yellow oil (0.82 g, 64%). $\delta_H$ (300 MHz; CDCl$_3$) 5.16 (1H, br m), (H$_3$C)C=CH$_a$H$_b$; 5.00 (1H, br m), (H$_3$C)C=CH$_a$H$_b$; 3.47 (4H, br m), 2×CH$_2$; 3.04 (3H, m), N(CH$_3$); 2.87 (3H, m), N(CH$_3$); 1.93 (3H, br m), CH$_3$; 1.43 (9H, s), C(CH$_3$)$_3$. $\delta_C$ (75.4 MHz; CDCl$_3$) 172.22, NOC(H$_3$C)C=CH$_2$; 155.21, NCO$_2$C(CH$_3$)$_3$; 140.42, (H$_3$C)C=CH$_2$; 115.21, (H$_3$C)C= CH$_2$; 79.01 C(CH$_3$)$_3$; 47.73, CH$_2$N(CH$_3$)OC(H$_3$C)C=CH$_2$; 44.99, CH$_2$N(CH$_3$)CO$_2$C(CH$_3$)$_3$; 36.94, CH$_2$N(CH$_3$)OC(H$_3$C)C=CH$_2$; 0.46,CH$_2$N(CH$_3$)CO$_2$C(CH$_3$)$_3$; 28.15, C(CH$_3$)$_3$; 20.15, CH$_3$. Found: M$^+$. 256.37.

N-t-BOC, N'-methacryloyl, N,N'-dimethyl-ethylenediamine (2.0 mmol, 0.51 g) was stirred in a solution of 3M HCl in ethyl acetate (2 cm$^3$) at room temperature for 30 min. The solution was then conc. in vacuo to give N'-methacryloyl, N,N'-dimethyl-ethylenediamine monohydrochloride as a clear yellow oil. This intermediate was stirred at room temperature in 2M NaOH for 10 min. The reaction mixture was then cooled to 0° C., and to this, was then added a solution of acryloyl chloride (2.2 mol, 0.18 cm$^3$) in chloroform (5 cm$^3$) dropwise, over 30 min. After the addition was complete, the reaction mixture was stirred at 0° C. for a further 1 h. The organic and aqueous phases were then separated, and the aqueous phase extracted with chloroform. The organic extracts were combined, dried (MgSO$_4$), filtered and conc. in vacuo, to give the crude product. The crude product was stirred at room temperature over a slurry of basic alumina in chloroform for 18 hr. Removal of the alumina and concentration of the filtrate then gave a pale yellow oil. Purification by flash chromatography (silica gel, diethyl ether:hexane:methanol elution) afforded N-acryloyl, N'-methacryloyl, N,N'-dimethyl-ethylenediamine as a yellow oil (0.20 g, 47%). (Spectroscopic data as above)

Example 8
Preparation of N-Acryloyl, N'-methacryloyl-ethylenediamine

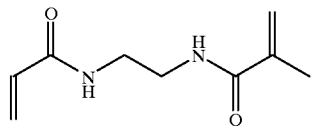

A solution of ethylenediamine (15 mmol, 10.1 cm$^3$) in water (150 cm$^3$) at 0° C. was adjusted to pH 8.5 with 3N HCl. To this, was added a solution of methacryloyl chloride (16.5 mmol, 16.1 cm$^3$) in chloroform (100 cm$^3$), dropwise, over 2 h. After the addition was complete, the reaction mixture was stirred at 0° C. for a further 2 h. The organic and aqueous layers were then separated, and the aqueous layer extracted with chloroform (3×50 cm$^3$). The aqueous layer was then collected and conc. in vacuo (freeze-dryer) to give a white solid. The residue was subjected to repeated fractional recrystallization from room temperature methanol, and the filtrate concentrated to give N-methacryloyl-ethylenediamine monohydrochloride as a clear, yellow oil (14.32 g, 58%). N-methacryloyl-ethylenediamine monohydrochloride (16 mmol, 20.0 g) was stirred in 2M NaOH (60 cm$^3$) for 10 min. This solution was subsequently diluted to a volume of 160 cm$^3$ with water, and stirred at 0° C. To this mixture was added a solution of acryloyl chloride (17.6 mmol, 14.3 cm$^3$) in chloroform (300 cm$^3$), dropwise, over 3 h. After the addition was complete, the reaction mixture was then stirred at 0° C. for a further 2 h. The organic and aqueous layers were separated, and the aqueous portion extracted with chloroform (3×100 cm$^3$). The organic extracts were combined and concentrated to give the crude product as a white solid. Recrystallization from acetonitrile then gave N-acryloyl, N'-methacryloyl-ethylenediamine as colorless needles (10.70 g, 37%), m.p. 140–142/C. $\delta_H$ (400 MHz; CDCl$_3$) 6.84 (1H, br s), N$\underline{H}$; 6.74 (1H, br m), N$\underline{H}$; 6.27 (1H, dd, J 16.9, 1.5 Hz), HC=C$\underline{H}_aH_b$; 6.13 (1H, dd, J 17.0, 10.2), $\underline{H}$C=CH$_a$H$_b$; 5.74 (1H, s), (H$_3$C)C=C$\underline{H}_a$H$_d$; 5.65 (1H, dd, J 10.3, 1.6 Hz), HC=CH$_a\underline{H}_b$; 5.34 (1H, br m), (H$_3$C)C=CH$_c\underline{H}_d$; 3.49 (4H, m), 2×C$\underline{H}_2$; 1.95 (3H, s), C$\underline{H}_3$. $\delta_C$ (75.4 MHZ:CDCl$_3$) 169.4, NHO$\underline{C}$(H$_3$C)C=CH$_2$; 167.0, NHO$\underline{C}$HC=CH$_2$; 139.2, (H$_3$C)$\underline{C}$=CH$_2$; 130.7, H$\underline{C}$=CH$_2$; 126.2, HC=$\underline{C}$H$_2$; 120.1, (H$_3$C)C=$\underline{C}$H$_2$; 40.4 $\underline{C}$H$_2$CH$_2$; 39.5, CH$_2\underline{C}$H$_2$; 18.4, $\underline{C}$H$_3$. Found: M$^+$. 182.1059.

Example 9
Preparation of Monomer Stock Solutions and SDS Gels

This example describes a general procedure for preparing stock solutions of acrylamide with a desired crosslinking agent. To ensure that the degree of crosslinking is equivalent to the corresponding acrylamide/BIS systems the amount of crosslinking agent is calculated on a mole:mole basis rather than a weight:weight basis.

1. Prepare monomer stock solutions of the following concentrations depending on the desired crosslinking agent concentration.

a) 30% T 3% C Dissolve 29.1 g acrylamide and 5.837× 10$^{-3}$ moles of crosslinking agent (equivalent to 0.9 g of BIS on a mole:mole basis) in 50 ml of distilled water and bring to a total volume of 100 ml.

b) 30% T 6% C Dissolve 28.2 g acrylamide and 11.67× 10$^{-3}$ moles of crosslinking agent (equivalent to 1.80 g of BIS) in 50 ml of distilled water and bring to a total volume of 100 ml.

2. Filter monomer solution through Whatmani No. 1 filter paper. Monomer stock solution may be stored at 40° C. for 2 to 3 months.

3. To the required amounts of water and 1.5M Tris HCl buffer are added the required aliquots of the 30% T monomer stock solution of the desired ° C. ratio (see Table 2, this being an example of the concentration range employed). Degas monomer solution under vacuum for 10 min at room temperature and then 10 min at 10° C.

4. Add 10% SDS solution, and then redox initiator system composed on freshly prepared 10% ammonium persulfate (10% AP, 200 1 l/ml) and 3-dimethylaminopropionitrile (DMAPN, 51 l/ml, except for 5% T 3% C stacking gel which is 101 l/ml) to monomer solution and swirl gently to mix.

TABLE 2

| ITEM | 5% T | 10% T | 15% T |
|---|---|---|---|
| water | 16.6 ml | 11.6 ml | 6.6 ml |
| 1.5M Tris buffer (pH 8.8) | 7.5 ml | 7.5 ml | 7.5 ml |
| acrylamide/monomer stock | 5.0 ml | 10.0 ml | 15.0 ml |
| 10% SDS | 0.300 ml | 0.300 ml | 0.300 ml |
| 10% ammonium persulfate | 0.600 ml | 0.600 ml | 0.600 ml |
| DMAPN | 30 µl | 15 µl | 15 µl |
| TOTAL VOLUME | 30 ml | 30 ml | 30 ml |

5. Using a syringe inject resolving gel solution slowly into prepared glass cassettes to a height of 75 mm, which are prepared as follows:

Glass cassettes are thoroughly cleaned with detergent and then allowed to air dry before being swabbed with ethanol or isopropanol to remove any grease or detergent film, and also to neutralise the surface of the glass. After cleaning, the sides and base of the cassettes are taped up using 3M Scotch electrical tape and then placed in a 60° C. oven for 1 hr.

The polyacrylamide gel is allowed to form (approx. 30 to 45 min) under an atmosphere of nitrogen. This nitrogen atmosphere is used for the polymerization procedure to ensure the absence of oxygen, thereby eliminating the appearance of "swirls" or "troughs" on polymerization.

6. Slowly apply a 5% T 3% C stacking gel onto the top of the resolving gel, which is also allowed to polymerize under an atmosphere of nitrogen.

7. Carefully remove the tape and wash the cassettes under water. Gels are then ready for electrophoresis. By this method it is possible to prepare vast range and size of well polymerized and optically transparent gels by varying the proportions of water and acrylamide/crosslinking agent stock solution.

Example 10
SDS-PAGE

This example describes a general procedure for performing SDS-PAGE with gels prepared in accordance with the invention.

1. Use a white surface when applying samples to the gels.
2. Insert gels into electrophoresis kit (which has been assembled according to manufacturers' instructions) and fill both reservoirs in the kit with SDS-PAGE running buffer or appropriate buffer. Place sample wells into the stacking gel at a depth of 1–2 mm.

3. Blow out any air bubbles appearing in the sample wells from above, using a plastic pipette.

4. Load approx. 10 μl of sample (eg. peptide or DNA marker) into the sample well using a microsyringe. Sample should "sit" nicely inside the well and be an intense blue colour. If too much sample is added, surrounding solution will go cloudy as the sample overflows from the well.

5. Electrophoresis is then performed noting that a 200V is maintained. current is between 150–40 mA and the process performed for the required time (60 minutes to days). The experiment is complete when the dye front reaches the bottom of the plate.

6. Remove sample spacers from the gel after approx. 2 min.

7. When electrophoresis is complete, the gel cassette may be removed and opened, and the gel eased off the cassette under running water.

8. The gel is washed into a vessel containing Coomassie Blue R-250 (0.25% coomassie blue, 40% methanol, 10% acetic acid) and stained for at least 30 min for proteins or ethidium bromide for DNA under known of the art conditions.

9. Gel is then destained (for proteins) by soaking in 40% methanol, 10% acetic acid overnight.

10. Gel is then sealed in to zip-lock bag, labelled and filed eg. in plastic pockets of a folder for reference.

Example 11

Comparison of Electrophoretic Performance with Standard BIS/Acrylamide Gels

In this example the performance of gels prepared in accordance with the present invention is compared to the performance of standard BIS/acrylamide gels. For the purpose of the comparison the asymmetrical crosslinking agents were substituted for BIS on a mole:mole basis rather than on a weight:weight basis to ensure equivalence in the number of reactive double bonds. The gels were compared by examining the migration velocity ($R_f$) of peptide and DNA markers in the respective gels, where $R_f$ is defined as:

$$R_f = \frac{\text{distance migrated by protein or DNA}}{\text{distance travelled by dye front}}$$

a) Preparation of Acrylamide/Crosslinking Agent Stock Solution

Stock solutions of acrylamide and the crosslinking agents were prepared to provide acrylamide/crosslinking agent stock solutions equivalent (on a mole:mole basis) with a 30% T 3% C acrylamide/BIS solution:

for BIS (Gel A);
  29.1 g of acrylamide and 0.90 g ($5.837 \times 10^{-3}$ moles) of crosslinking agent;
for N-acryloyl, N'-methacryloyl methylenediamine (Gel B);
  29.1 g of acrylamide and 0.98 g ($5.837 \times 10^{-3}$ moles) of crosslinking agent;
for N-acryloyl, N'-methacryloyl ethylenediamine (Gel C);
  29.1 g of acrylamide and 1.06 g ($5.837 \times 10^{-3}$) moles of crosslinking agent; and
for methacrylethylacrylamide (Gel D);
  29.1 g of acrylamide and 1.07 g ($5.837 \times 10^{-3}$ moles of crosslinking agent.

b) Preparation of Gels

Gels were prepared from the stock solutions in accordance with Table 3 below.

TABLE 3

| Major Components | 10% T 3% C* | 15% T 3% C* |
|---|---|---|
| Water | 11.6 ml | 6.6 ml |
| 1.5M Tris Buffer pH 8.8 | 7.5 ml | 7.5 ml |
| Stock Solution | 10.0 ml | 15.0 ml |
| 10% SDS | 0.300 ml | 0.300 ml |
| 10% ammonium persulfate | 0.600 ml | 0.600 ml |
| DMAPN | 15 μl | 15 μl |
| Total Volume | 30 ml | 30 ml |

*These weight based concentrations of acrylamide and crosslinking agent are only correct when BIS is employed as the crosslinking agents. When a crosslinking agent other than BIS is employed, the amount of crosslinking agent is the mole:mole equivalent of BIS required to give these concentrations.

c) Assessment of Electrophoretic Performance

Figure 2:
FIG. 2 shows the separation of the same standard protein mixture of FIG. 1 where the concentrations of acrylamide and crosslinking agent are equivalent, on a mole:mole basis, with a 15% T 3% C BIS gel.
Figure 2:
Figure 2:
Figure 2:

The stained gels shown in FIGS. 1 and 2 were obtained after performing electrophoresis under the standard conditions with a commercially available standard molecular weight protein marker system composed of (1) myosin (200,000), (2), β-galactosidase (116,250), (3) phosphorylase b (97,400), (4) bovine serum albumin (66,200), (5) ovalbumin (45,000), (6) carbonic anhydrase (31,000), (7) soybean trypsin inhibitor (21,5000), (8) lysozyme (14,400) and (9) aprotinin (6,500). The gels contain the following crosslinking gents: (Gel A) methylene-bisacrylamide (BIS), (Gel B) N-acryloyl, N'-methacryloyl methylenediamine, (Gel C) N-acryloyl, N'-methacryloyl ethylenediamine and (Gel D)2-methacrylethylacrylamide.

(i) 10% T 3% C gels

The 10% T 3% C gels prepared and stained as described above are shown in figure I. It is clear from a comparison of the stained gels that equivalent proteins move through the gels incorporating the asymmetrical crosslinking agents (Gels B, C and D) at a faster rate, ie. have a higher migration or Rf value, than through the standard BIS gel (Gel A). There also appears to be differences in the degree of separation between specific protein bands such that these new gels may be used in a manner to achieve a maximum of separation and resolution within a particular molecular weight region. For example, a 10% T 3% C gel incorporating N-acryloyl, N'-methacryloyl methylenediamine (Gel B) exhibits an improved separation for the protein bands in the region 116,250 to 66,200, which is similarly observed for the Gels C and D. Each of Gels B. C and D showed enhanced performance in the separation of the high molecular weight components of the marker system, while remaining optically transparent.

(ii) 15% T 3% gels

The 15% T 3% C gels prepared and stained described above are shown in figure 2.

As with the 10% T 3% gels described above, these 15% T 3% C gels incorporating asymmetrical crosslinking agents (Gels B, C and D) afforded improved electrophoretic separations compared to the BIS gel (Gel A). The improved separation is evident for both the high and low molecular weight components.

These results show an enhanced separation and improved resolution, while still maintaining optical transparency. For example, the 15% T 3% C gel incorporating the crosslinking agent N-acryloyl, N'-methacryloyl methylenediamine (Gel B) exhibits an enhanced separation in the region 66,000 to 21,500. Similar results are observed for the gels containing the other asymmetrical crosslinking agents (Gels C and D).

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of separating molecules comprising providing a cross-linked polymer gel comprising a cross-linking moiety of the formula:

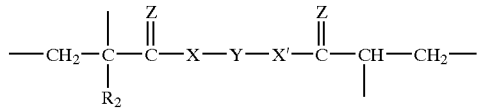

wherein

X and X' are independently selected from the group consisting of —O—, —O— and —NR—, where R is H, alkyl or cycloalkyl, Y is an optionally substituted non-aromatic divalent linking group, Z is O or S; and $R_2$ is a $C_1$–$C_4$ alkyl group, provided that when said crosslinked polymer gel is a non-aqueous polymer gel and $R_2$ is $CH_3$ and Y is —$CH_2$—$CH_2$—, X, X' and Z are not all O, placing a sample containing the molecules to be separated onto the gel, and subjecting the gel and sample to a separation technique.

2. A method according to claim 1 wherein the separation technique is electrophoresis.

3. A method according to claim 1 wherein the sample includes a biomolecule selected from proteins, enzymes, peptides, oligo- or polynucleotides and carbohydrates.

* * * * *